US010106604B2

(12) United States Patent
Gram et al.

(10) Patent No.: US 10,106,604 B2
(45) Date of Patent: *Oct. 23, 2018

(54) METHOD OF TREATING AUTO-INFLAMMATORY SYNDROMES WITH IL-1BETA ANTIBODIES RELATED TO CANAKINUMAB

(71) Applicant: Novartis AG, Basel (CH)

(72) Inventors: Hermann Gram, Weil am Rhein (DE); Thomas Jung, Vienna (AT)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/359,784

(22) Filed: Nov. 23, 2016

(65) Prior Publication Data

US 2017/0073411 A1    Mar. 16, 2017

Related U.S. Application Data

(60) Division of application No. 14/861,191, filed on Sep. 22, 2015, now Pat. No. 9,534,047, which is a continuation of application No. 13/955,673, filed on Jul. 31, 2013, now Pat. No. 9,168,298, which is a continuation of application No. 13/587,978, filed on Aug. 17, 2012, now Pat. No. 8,524,667, which is a continuation of application No. 12/601,280, filed as application No. PCT/EP2008/056520 on May 28, 2008, now Pat. No. 8,282,922.

(30) Foreign Application Priority Data

May 29, 2007  (EP) .................................. 07109084

(51) Int. Cl.
 *C07K 16/24* (2006.01)
 *A61K 39/395* (2006.01)
 *A61K 39/00* (2006.01)

(52) U.S. Cl.
 CPC ........ *C07K 16/245* (2013.01); *A61K 39/3955* (2013.01); *A61K 2039/505* (2013.01); *C07K 2317/21* (2013.01); *C07K 2317/565* (2013.01); *C07K 2317/76* (2013.01); *C07K 2317/92* (2013.01)

(58) Field of Classification Search
 None
 See application file for complete search history.

(56) References Cited

U.S. PATENT DOCUMENTS

| 5,643,915 A | 7/1997 | Andrulis, Jr. et al. |
| 7,695,718 B2 | 4/2010 | Solinger et al. |
| 2008/0286266 A1 | 11/2008 | Lowe et al. |

FOREIGN PATENT DOCUMENTS

| EP | 0720849 | 10/1996 |
| WO | 200216436 | 2/2002 |
| WO | WO02/16436 A2 | 2/2002 |
| WO | 2004005310 | 1/2004 |
| WO | WO 2004/035607 A2 | 4/2004 |
| WO | 2005000215 | 1/2005 |
| WO | 2005082070 | 9/2005 |
| WO | WO 2005/117945 A1 | 12/2005 |
| WO | WO2007/002261 A2 | 1/2007 |
| WO | 2007042524 | 4/2007 |
| WO | 2007050607 | 5/2007 |

OTHER PUBLICATIONS

Beiboer et al., (Guided Selection of a Pan Carcinoma Specific Antibody Reveals Similar Binding Characteristics yet Structural Divergence Between the Original Murine Antibody and its Human Equivalent, J. Mol. Biol. 296, 833-849, 2000. (Year: 2000).*
Rader et al. (A phage display approach for rapid antibody humanization: Designed combinatorial V gene libraries, PNAS 95, 8910-8915, 1998. (Year: 1998).*
Pay et al., "Synovial proinflammatory cytokines and their correlation. with matrix metalloproteinase-3 expression in Behcer's disease. Does interleukin-1Beta play a major role in Behcet's synovitis?", Rheumatol. Int., 2006, vol. 26, p. 608-613.
Hoffman et al., The first placebo-controlled trial in cryopyrin-associated periodic syndromes (CAPS): IL-1 trap (rilonacept) markedly reduces clinical and laboratory abnormalities in patients with familial and cold autoinflammatory syndrome (FCAS) and muckle-wells syndrome (MWS):, Journal of Allergy and Clinical Immunology, Mosby-Yearly Book, Inc., vol. 119, No. 2, pp. 524, (Feb. 2007).
So et al., "A pilot study of IL-1 inhibition by anakinra in acute gout", arthritis Research and Therapy, Biomed, vol. 9, No. 2, pp. R28, (Mar. 12, 2007).
Martinon et al., "Gout-associated uric acid crystals activate the NALP3 inflammasome", Nature, vol. 440, No. 7081, pp. 237-241, (Mar. 9, 2006).
Portolano et al., "Lack of Promiscuity in Autoantigen-Specific H and L Chain Combinations as Revealed by Human H and L Chain Roulette", J. Immunol., vol. 150, No. 3, pp. 880-887, 1993.
Clackson et al., "Making antibody fragments using phage display libraries", Nature, vol. 352, pp. 624-628, 1991.

(Continued)

*Primary Examiner* — Elly-Gerald Stoica
(74) *Attorney, Agent, or Firm* — Jim Lynch

(57) ABSTRACT

This invention relates to a novel use of IL-1β-ligand/IL-1 receptor disrupting compounds (herein referred to as "IL-1 beta Compounds"); such as small molecular compounds disrupting IL-1b ligand-IL-1 receptor interaction, IL-1b antibodies or IL-1 receptor antibodies, e.g. IL-1b binding molecules described herein, e.g. antibodies disclosed herein, e.g. IL-1b binding compounds or IL-1 receptor binding compounds, and/or RNA compounds decreasing either IL-1b ligands or IL-1 receptor protein levels, in the treatment and/or prevention of auto-inflammatory syndromes, e.g. Juvenile rheumatoid arthritis or adult rheumatoid arthritis syndrome and to methods of treating and/or preventing auto-inflammatory syndromes, e.g. Juvenile rheumatoid arthritis or adult rheumatoid arthritis syndrome, in mammals, particularly humans.

18 Claims, No Drawings

Specification includes a Sequence Listing.

(56) References Cited

OTHER PUBLICATIONS

Rudikoff et al., "Single amino acid substitution altering antigen-binding specificity", Proc. Natl. Acad. Sci, USA, vol. 79, pp. 1979-1983, 1982.
Lachmann et al., "(7) Muckle Wells syndrome—the paradigm of an IL-1BETA-driven disease:insights from treatment", QJM: An International Journal of Medicine, vol. 99, No. 114, Nov. 2008,pp. 788-789.
Larsen Clause M et al., "Interleukin-1-receptor antagonist in type 2 diabetes mellitus", New England Journal of Medicine, vol. 356, No. 15, Apr. 12, 2007 pp. 1517-1526.
"Efficacy and Safety of a Single Dose of Canakinumab (ACZ885) in Hospitalized Patients with Acute Gout", ClinicalsTrial.gov Identifier: NCT00663169, Clinicaltrial.gov, p. 1-4, Downloaded from http://www.clinicaltrials.gov/ct2/show/NCT00663169?term=canakinumab+gout&rank+9 on Mar. 26, 2013.
"Long Term Study of Canakinumab (ACZ885) in Patients With Gout", ClinicalTrials.gov Identifier: NCT00927810, p. 1-3, Downloaded from http://www.clinicaltrials.gov/ct2/show/NCT009278107term=acz885+gout&rank=4 on Mar. 25, 2013.
"Evaluating Efficacy of canakinumab (ACZ885) in Prevention of Acute Flares in Chronic Gout Patients initiating Allopurinol Therapy", ClinicalTrials.gov identifier: NCT00819585, p. 1-5, Downloaded from http://www.clinicaltrials.gov/ct2/show/NCT00819585?term=acz885+gout&rank=1 on Mar. 25, 2013.
Schlesinger et al."Canakinumab for acute gouty arthritis in patients with limited treatment options: results from two randomised, multicentre active-controlled, double-blind trials and their initial extensions", Ann Rheum Dis, pp. 1-10, published on line at http://ard.bmj.com/content/early/2012/05/14/annrheumdis-2011-200908.full.html (May 14, 2012) Downloaded from ard.bmj.com on Sep. 5, 2012—Published by group.bmj.com.
Schlesinger et al., "Canakinumab relieves symptoms of acute flares and improves health-related quality of life in patients with difficult-to-treat Gouty Arthritis by suppressing inflammation: results of a randomized, dose ranging study", Arthristis Research & Therapy, 13:R53, (2011).
Reginato A.M., Olsen B.R., "Genetics and experimental models of crystal-induced arthritis. Lessons learned from mice and men: is it crystal clear?", Curr. Opin Rheumatol., Mar.;19(2):134-45, 2007.
Rabinovitch A., "An Update on Cytokines in the Pathogenesis of Insulin-dependent Diabetes Mellitus", Diabetes Metab. Rev., vol. 14, pp. 129-151, (1998).
Chen et al.,"MyD88-dependent IL-1 receptor signaling is essential for gouty inflammation stimulated by monosodium urate crystals", J. Clin. Investig., vol. 116, pp. 2262-2271, (2006).
Alexandraki K. et al., "Inflammatory Process in Type 2 Diabetes. The Role of Cytokines", Ann. N.Y. Acad. Sci., vol. 1084, pp. 89-117 (2006).
Kolb H. et al., "An immune origin of type 2 diabetes?", Diabetologia, vol. 48, pp. 1038-1050, (2005).
Ziegler D., "Type 2 Diabetes As An Inflammatory Cardiovascular Disorder", Current Molecular Medicine, vol. 5, pp. 309-322, (2005).
Simon A. et al., Pathogenesis of familial periodic fever syndromes or hereditary autoinflammatory syndromes, Am J Physiol Regul Integr Comp Physiol, vol. 292, pp. R86-R98, (2007).
Sacré K. et al., "Dramatic improvement following interleukin 1beta blockade in tumor necrosis factor receptor-1-associated syndrome (TRAPS) resistant to anti-TNF-alpha therapy", J Rheumatol, vol. 35; pp. 357-358, (2008).
Farasat S. et al. "Autoinflammatory Diseases", Archives of Dermatology, vol. 144 (No. 3), pp. 392-402, (Mar. 2008).
Stojanov S. et al., "Familial autoinflammatory diseases: genetics, pathogenesis and treatment", Current Opinion in Rheumatology, vol. 17, pp. 586-599, (2005).
Adams et al., "Pathophysiology of Atherosclerosis: Development, Regression, Restenosis", Current Atherosclerosis Reports, vol. 2, pp. 251-258, (2000).
Terkeltaub R., "Gout in 2006 The Perfect Storm," Bulletin of the NYU Hospital for joint Diseases, vol. 64, No. 1 & 2 pp. 82-86, 2006.
Warner et al., "Human Interleukin 1 induces Interleukin 1 gene expression in human vascular smooth muscle cell", J. Exp. Med., vol. 165, pp. 1316-1331, May 1987.
Dinarello, "The Many Worlds of Reducing Interleukin-1", Arthritis and Rheumatism, 2005, vol. 52, No. 7, pp. 1960-1967.
Printout of EudraCT No. 2015-003763-11 (CACZ885D2208), dated Jul. 18, 2016.
Church et al., "Hereditary auto-inflammatory disorders and biologics", Springer Semin Immunopathol, vol. 27, pp. 494-508, 2006.
"An IL-1 Family Member Requires Caspase-1 Processing and Signals through the ST2 Receptor", Immunity, vol. 23, pp. 461-462, 2005.
Simon A. et al., "Beneficial response to interleukin 1 receptor antagonist in traps", The American Journal of Medicine, 2004, vol. 117: 208-210.

* cited by examiner

```
                          SEQUENCE LISTING

<160> NUMBER OF SEQ ID NOS: 14

<210> SEQ ID NO 1
    <211> LENGTH: 118
    <212> TYPE: PRT
    <213> ORGANISM: homo sapiens

<400> SEQUENCE: 1

Gln Val Gln Leu Val Glu Ser Gly Gly Gly Val Val Gln Pro Gly Arg
    1               5                   10                  15

Ser Leu Arg Leu Ser Cys Ala Ala Ser Gly Phe Thr Phe Ser Val Tyr
                20                  25                  30

Gly Met Asn Trp Val Arg Gln Ala Pro Gly Lys Gly Leu Glu Trp Val
                35                  40                  45

Ala Ile Ile Trp Tyr Asp Gly Asp Asn Gln Tyr Tyr Ala Asp Ser Val
        50                  55                  60

Lys Gly Arg Phe Thr Ile Ser Arg Asp Asn Ser Lys Asn Thr Leu Tyr
    65                  70                  75                  80

Leu Gln Met Asn Gly Leu Arg Ala Glu Asp Thr Ala Val Tyr Tyr Cys
                85                  90                  95

Ala Arg Asp Leu Arg Thr Gly Pro Phe Asp Tyr Trp Gly Gln Gly Thr
                100                 105                 110

Leu Val Thr Val Ser Ser
                115

<210> SEQ ID NO 2
    <211> LENGTH: 107
    <212> TYPE: PRT
    <213> ORGANISM: Homo sapiens

<400> SEQUENCE: 2

Glu Ile Val Leu Thr Gln Ser Pro Asp Phe Gln Ser Val Thr Pro Lys
    1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
                35                  40                  45

Lys Tyr Ala Ser Gln Ser Phe Ser Gly Val Pro Ser Arg Phe Ser Gly
        50                  55                  60

Ser Gly Ser Gly Thr Asp Phe Thr Leu Thr Ile Asn Ser Leu Glu Ala
    65                  70                  75                  80

Glu Asp Ala Ala Ala Tyr Tyr Cys His Gln Ser Ser Ser Leu Pro Phe
                85                  90                  95

Thr Phe Gly Pro Gly Thr Lys Val Asp Ile Lys
                100                 105

<210> SEQ ID NO 3
    <211> LENGTH: 5
    <212> TYPE: PRT
    <213> ORGANISM: ARTIFICIAL
```

<220> FEATURE:
<223> OTHER INFORMATION: CDR

<400> SEQUENCE: 3

Val Tyr Gly Met Asn
1               5

<210> SEQ ID NO 4
<211> LENGTH: 17
<212> TYPE: PRT
<213> ORGANISM: ARTIFICIAL
<220> FEATURE:
<223> OTHER INFORMATION: CDR

<400> SEQUENCE: 4

Ile Ile Trp Tyr Asp Gly Asp Asn Gln Tyr Tyr Ala Asp Ser Val Lys
1               5                   10                  15

Gly

<210> SEQ ID NO 5
<211> LENGTH: 6
<212> TYPE: PRT
<213> ORGANISM: ARTIFICIAL
<220> FEATURE:
<223> OTHER INFORMATION: CDR

<400> SEQUENCE: 5

Asp Leu Arg Thr Gly Pro
1               5

<210> SEQ ID NO 6
<211> LENGTH: 11
<212> TYPE: PRT
<213> ORGANISM: ARTIFICIAL
<220> FEATURE:
<223> OTHER INFORMATION: CDR

<400> SEQUENCE: 6

Arg Ala Ser Gln Ser Ile Gly Ser Ser Leu His
1               5                   10

<210> SEQ ID NO 7
<211> LENGTH: 6
<212> TYPE: PRT
<213> ORGANISM: ARTIFICIAL
<220> FEATURE:
<223> OTHER INFORMATION: CDR

<400> SEQUENCE: 7

Ala Ser Gln Ser Phe Ser
1               5

<210> SEQ ID NO 8
<211> LENGTH: 7
<212> TYPE: PRT
<213> ORGANISM: ARTIFICIAL
<220> FEATURE:
<223> OTHER INFORMATION: CDR

<400> SEQUENCE: 8

His Gln Ser Ser Ser Leu Pro
1               5

<210> SEQ ID NO 9
<211> LENGTH: 5
<212> TYPE: PRT

```
<213> ORGANISM: ARTIFICIAL
<220> FEATURE:
<223> OTHER INFORMATION: CDR

<400> SEQUENCE: 9

Ser Tyr Trp Ile Gly
1               5

<210> SEQ ID NO 10
<211> LENGTH: 17
<212> TYPE: PRT
<213> ORGANISM: ARTIFICIAL
<220> FEATURE:
<223> OTHER INFORMATION: CDR

<400> SEQUENCE: 10

Ile Ile Tyr Pro Ser Asp Ser Asp Thr Arg Tyr Ser Pro Ser Phe Gln
1               5                   10                  15

Gly

<210> SEQ ID NO 11
<211> LENGTH: 9
<212> TYPE: PRT
<213> ORGANISM: ARTIFICIAL
<220> FEATURE:
<223> OTHER INFORMATION: CDR

<400> SEQUENCE: 11

Tyr Thr Asn Trp Asp Ala Phe Asp Ile
1               5

<210> SEQ ID NO 12
<211> LENGTH: 9
<212> TYPE: PRT
<213> ORGANISM: ARTIFICIAL
<220> FEATURE:
<223> OTHER INFORMATION: CDR

<400> SEQUENCE: 12

Gln Gln Arg Ser Asn Trp Met Phe Pro
1               5

<210> SEQ ID NO 13
<211> LENGTH: 11
<212> TYPE: PRT
<213> ORGANISM: ARTIFICIAL
<220> FEATURE:
<223> OTHER INFORMATION: CDR

<400> SEQUENCE: 13

Arg Ala Ser Gln Ser Val Ser Ser Tyr Leu Ala
1               5                   10

<210> SEQ ID NO 14
<211> LENGTH: 7
<212> TYPE: PRT
<213> ORGANISM: ARTIFICIAL
<220> FEATURE:
<223> OTHER INFORMATION: CDR

<400> SEQUENCE: 14

Asp Ala Ser Asn Arg Ala Thr
1               5
```

METHOD OF TREATING AUTO-INFLAMMATORY SYNDROMES WITH IL-1BETA ANTIBODIES RELATED TO CANAKINUMAB

This is a divisional of U.S. patent application Ser. No. 14/861,191, filed Sep. 22, 2015, which is a continuation of U.S. patent application Ser. No. 13/955,673, filed Jul. 31, 2013, which issued as U.S. Pat. No. 9,168,298 on Oct. 27, 2015, which is a continuation of U.S. patent application Ser. No. 13/587,978, filed Aug. 17, 2012, which issued as U.S. Pat. No. 8,524,667 on Sep. 3, 2013, which is a continuation of U.S. patent application Ser. No. 12/601,280, filed Nov. 23, 2009 and which issued as U.S. Pat. No. 8,282,922 on Oct. 9, 2012, which is a National Stage of International Application No. PCT/EP08/056520 filed on May 28, 2008, which claims benefit of European Application No. 07109084.9 filed May 29, 2007, which in its entirety are herein incorporated by reference.

BACKGROUND OF THE DISCLOSURE

This invention relates to a novel use of IL-1β-ligand/IL-1 receptor disrupting compounds (herein referred to as "IL-1beta Compounds"); such as small molecular compounds disrupting IL-1β ligand IL-1 receptor interaction, IL-1β antibodies or IL-1 receptor antibodies, e.g. IL-1β binding molecules described herein, e.g. antibodies disclosed herein, e.g. IL-1β binding compounds or IL-1 receptor binding compounds, and/or RNA compounds decreasing either IL-1β ligands or IL-1 receptor protein levels, in the treatment and/or prevention of auto-inflammatory syndromes, e.g. Juvenile rheumatoid arthritis or adult rheumatoid arthritis syndrome and to methods of treating and/or preventing auto-inflammatory syndromes, e.g. Juvenile rheumatoid arthritis or adult rheumatoid arthritis syndrome, in mammals, particularly humans.

Interleukin-1β (IL-1beta or IL-1β or Interleukin-1β have the same meaning herein) is a potent immuno-modulator which mediates a wide range of immune and inflammatory responses. Inappropriate or excessive production of IL-1β is associated with the pathology of various diseases and disorders, such as septicemia, septic or endotoxic shock, allergies, asthma, bone loss, ischemia, stroke, traumatic brain injury, rheumatoid arthritis and other inflammatory disorders. Antibodies to IL-1β have been proposed for use in the treatment of IL-1 mediated diseases and disorders; see for instance, WO 95/01997 and the discussion in the introduction thereof and WO 02/16436, the content of which is incorporated by reference.

SUMMARY OF THE DISCLOSURE

In accordance with the present invention, it has now surprisingly been found that IL-1beta compounds are useful in the prevention and treatment of Auto-Inflammatory Syndromes in patients such as in mammals, particularly humans. Auto-Inflammatory Syndromes according to the inventions are e.g., but not limited to, a group of inherited disorders characterized by recurrent episodes of inflammation, that in contrast to the auto-immune diseases lack high-titer autoantibodies or antigen specific T cells. Furthermore, Auto-inflammatory Syndromes according to the inventions show increased IL-1beta secretion (loss of negative regulatory role of pyrin which seems mutated in said diseases), NFkB activation and impaired leukocyte apoptosis). Auto-inflammatory Syndromes according to the inventions are Muckle-Wells syndromes (MWS), LADA (Latent Autoimmune Diabetes in Adults), familial cold autoinflammmatory syndrome (FCAS), Cryopyrin-associated periodic syndromes (CAPS), neonatal-onset multisystem inflammatory syndrome (NOMID), chronic infantile neurological, cutaneous, articular (CINCA) syndrome, familial Mediterranean fever (FMF) and/or certain form of juvenile arthritis such as systemic onset juvenile idiopathic arthritis (SJIA), certain form of juvenile rheumatoid arthritis such as systemic onset juvenile idiopathic rheumatoid arthritis and/or certain form of adult rheumatoid arthritis. The IL-1beta compounds may also be useful in the treatment of type 2 diabetes, where clinical and preclinical studies show improved islet function by IL-1 blockade. IL-1beta compounds are also be useful in the treatment of various diabetes related pathologies such as retinopathy, wound healing, vascular diseases, (incl. arterial restenosis after stenting or angioplasty), renal dysfunction, chronic kidney disease and metabolic syndrome and obesity. The IL-1beta compounds may also be useful in the treatment of migraine, synovitis, gout, pseudogout/gouty arthritis or chondrocalcinosis, chronic obstructive pulmonary disease (COPD), ventilation induced lung damage, various pain conditions, such as morphine resistant pain, neuropathic pain, pre-term birth pain, discogenic pain, inflammatory pain, headache, or migraine. IL-1beta is involved in pain perception and amplifies neurogenic signals. Furthermore IL-1beta compounds of the invention are useful in the treatment of atherosclerosis, acute renal colic, biliary colic and pain related to these disorders.

The IL-1beta compounds may be useful in the treatment of Periodic Fever Syndromes: Familial Mediterranean Fever (FMF), Tumor Necrosis Factor Receptor Associated Periodic Syndrome (TRAPS), Hyperimmunoglobulin D syndrome (HIDS), also called Mevalonate Kinase Associated Periodic Fever Syndrome, Familial Cold auto inflammatory syndrome and Periodic fever, Aphthous-stomatitis, Pharyngitis, Adenitis (PFAPA) Syndrome, where IL-1beta is a dominant cytokine. Other diseases wherein IL-1beta is a dominant cytokine and that can be treated with IL-1beta compounds according to the invention comprise Anti-synthetase syndrome, Macrophage activation syndrome MAS, Behcet Disease, Blau's syndrome, PAPA syndrome, Schnizler's syndrome, Sweet's syndrome. IL-1beta ligand-receptor blocking and IL-1beta compounds of the invention may also be used to treat Vasculitides; Giant-cell arteritis (GCA), Henoch-Schoenlein purpura, Primary systemic vasculitis, Kawasaki disease (mucocutaneous lymph node syndrome), Takayasu arteritis, Polyarteritis nodosa, Essential cryoglobulinemic vasculitis, microscopic polyangiitis (MPA) and Churg-Strauss syndrome (CSS), urticarial vasculitis. Furthermore IL-1beta compounds of the invention are useful in the treatment of autoimmune diseases like sarcoidosis, pemphygus, ankylosing spondylitis, Alzheimer disease, amyloidosis, secondary amyloidosis and adult onset Still disease (AOSD). IL-1beta compounds of the invention may be used to treat HLA-B27 associated diseases such as but not limited to psoriatica, spondylitis ankylosans, Morbus Reiter and enteropathic arthritis. IL-1beta compounds according to the invention may be used to treat rheumatic fever, polymyalgia rheumatica and giant cell artheriitis. Finally IL-1beta compounds of the invention may be used to treat infections, in particular bacterial infections and viral infections, more in particular bacterial infections associated with arthritic symptoms or observations, such as but not limited to hematogenic osteomyelitis, infectious arthritis, tuberculotic arthritis.

Preferably the IL-1beta Compounds are useful in the prevention and treatment of Juvenile rheumatoid arthritis and adult rheumatoid arthritis and/or Muckle Wells Syndrome.

DETAILED DESCRIPTION OF THE DISCLOSURE

In accordance with the particular findings of the present invention, the following embodiments are provided:

The present invention concerns compositions and methods for the prevention and treatment of Auto-Inflammatory Syndromes in mammals, including humans. Accordingly, the IL-1beta Compounds are also useful to prepare medicines and medicaments for the treatment of Auto-inflammatory Syndromes. In a specific aspect, such medicines and medicaments comprise a therapeutically effective amount of IL-1beta Compounds with a pharmaceutically acceptable carrier.

In another embodiment, the invention provides the use of an antibody which specifically binds to any of the above or below described polypeptides, e.g. IL-1β ligand or IL-1β receptor, preferably IL-1β ligand, in the prevention and/or treatment of Juvenile rheumatoid arthritis or adult rheumatoid arthritis syndrome and/or other Auto-Inflammatory Syndromes and/or Muckle Wells Syndrome. Optionally, the antibody is a monoclonal antibody, humanized antibody, antibody fragment or single-chain antibody. In one aspect, the present invention concerns an isolated antibody which binds a IL-1β ligand. In another aspect, the antibody inhibits or neutralizes the activity of a IL-1β ligand (an antagonist antibody). In another aspect, the antibody is a monoclonal antibody, which has either a human or nonhuman complementarily determining region (CDR) residues and human framework region (FR) residues. The antibody may be labeled and may be immobilized on a solid support. In a further aspect, the antibody is an antibody fragment, a monoclonal antibody, a single-chain antibody, or an anti-idiotypic antibody. In yet another embodiment, the present invention provides a composition comprising an anti-IL-1β ligand or IL-1β receptor antibody, preferably an anti-IL-1β ligand antibody, in a mixture with a pharmaceutically acceptable carrier. In one aspect, the composition comprises a therapeutically effective amount of the antibody. Preferably, the composition is sterile. The composition may be administered in the form of a liquid pharmaceutical formulation, which may be preserved to achieve extended storage stability. Alternatively, the antibody is a monoclonal antibody, an antibody fragment, a humanized antibody, or a single-chain antibody.

In another embodiment, the invention provides the use of IL-1beta Compounds, e.g. IL-1beta antibody, which are capable to interrupt the positive IL-1beta feedback loop in vivo; in the prevention and/or treatment of Juvenile rheumatoid arthritis or adult rheumatoid arthritis and/or other Auto-Inflammatory Syndromes and/or Muckle Wells Syndrome. This positive feedback in vivo leads to self-sustained overproduction of IL-1b in these patients.

In another embodiment, the invention provides the use of an IL-1beta Compounds, e.g. IL-1beta antibody, in diseases with a mutation in the MEFV gene, located on chromosome 16p13 and which codes for the protein pyrin (also known as marenostrin). Pyrin is expressed in granulocytes, monocytes and synovial fibroblasts. Pyrin is involved in IL-1beta processing.

In a further embodiment, the invention concerns an article of manufacture, comprising: (a) a composition of matter comprising an anti-IL-1 beta ligand or IL-1beta receptor antibody, preferably an anti-IL-1β ligand antibody; (b) a container containing said composition; and (c) a label affixed to said container, or a package insert included in said container referring to the use of said anti-IL-1β ligand or IL-1β receptor antibody, preferably an anti-IL-1β ligand antibody, in the treatment of Juvenile rheumatoid arthritis or adult rheumatoid arthritis and/or other Auto-Inflammatory Syndromes and/or Muckle Wells Syndrome. The composition may comprise a therapeutically effective amount of an anti-IL-1β ligand or IL-1β receptor antibody, preferably an anti-IL-1β ligand.

In yet a further embodiment, the invention provides a method or use as defined above, comprising co-administration of a therapeutically effective amount of IL-1beta Compounds in free form or salt form, preferably in a pharmaceutically acceptable delivery form such as intravenously or subcutaneously, and a second drug substance, said second drug substance being an Anti-inflammatory Compound in free form or salt form.

In yet a further embodiment, an IL-1beta Compounds used according to the invention is an IL-1β binding molecule which comprise an antigen binding site comprising at least one immunoglobulin heavy chain variable domain ($V_H$) which comprises in sequence hypervariable regions CDR1, CDR2 and CDR3, said CDR1 having the amino acid sequence Val-Tyr-Gly-Met-Asn (SEQ ID NO:3), said CDR2 having the amino acid sequence Ile-Ile-Trp-Tyr-Asp-Gly-Asp-Asn-Gln-Tyr-Tyr-Ala-Asp-Ser-Val-Lys-Gly (SEQ ID NO:4), and said CDR3 having the amino acid sequence Asp-Leu-Arg-Thr-Gly-Pro (SEQ ID NO:5); and direct equivalents thereof.

In yet a further embodiment, an IL-1beta Compound used according to the invention is an IL-1β binding molecule which comprise at least one immunoglobulin light chain variable domain ($V_L$) which comprises in sequence hypervariable regions CDR1', CDR2' and CDR3', said CDR1' having the amino acid sequence Arg-Ala-Ser-Gln-Ser-Ile-Gly-Ser-Ser-Leu-His (SEQ ID NO:6) said CDR2' having the amino acid sequence Ala-Ser-Gln-Ser-Phe-Ser (SEQ ID NO:7) and said CDR3' having the amino acid sequence His-Gln-Ser-Ser-Ser-Leu-Pro (SEQ ID NO:8) and direct equivalent thereof.

In yet a further embodiment, an IL-1beta Compound used according to the invention is a single domain IL-1beta binding molecule comprising an isolated immunoglobulin heavy chain comprising a heavy chain variable domain ($V_H$) as defined above, e.g. for the preparation of a medicament for the treatment of Juvenile rheumatoid arthritis or adult rheumatoid arthritis syndrome and/or other Autoinflammatory Syndromes, preferably Juvenile rheumatoid arthritis or adult rheumatoid arthritis syndrome and/or Muckle Wells Syndrome.

In yet a further embodiment, an IL-1beta Compound used according to the invention is an IL-1β binding molecule comprising both heavy ($V_H$) and light chain ($V_L$) variable domains in which said IL-1β binding molecule comprises at least one antigen binding site comprising:

a) an immunoglobulin heavy chain variable domain ($V_H$) which comprises in sequence hypervariable regions CDR1, CDR2 and CDR3, said CDR1 having the amino acid sequence Val-Tyr-Gly-Met-Asn (SEQ ID NO:3), said CDR2 having the amino acid sequence Ile-Ile-Trp-Tyr-Asp-Gly-Asp-Asn-Gln-Tyr-Tyr-Ala-Asp-Ser-Val-Lys-Gly (SEQ ID NO:4), and said CDR3 having the amino acid sequence Asp-Leu-Arg-Thr-Gly-Pro (SEQ ID NO:5), and b) an immunoglobulin light chain variable domain (V$_L$) which comprises in sequence hypervariable regions CDR1', CDR2' and CDR3', said CDR1' having the amino acid sequence Arg-Ala-Ser-Gln-Ser-Ile-Gly-Ser-Ser-Leu-His (SEQ ID NO:6), said CDR2' having the amino acid sequence Ala-Ser-Gln-Ser-Phe-Ser (SEQ ID NO:7), and said CDR3' having the amino acid sequence His-Gln-Ser-Ser-Ser-Leu-Pro (SEQ ID NO:8);

and direct equivalents thereof.

Unless otherwise indicated, any polypeptide chain is herein described as having an amino acid sequence starting at the N-terminal extremity and ending at the C-terminal extremity.

When the antigen binding site comprises both the V$_H$ and V$_L$ domains, these may be located on the same polypeptide molecule or, preferably, each domain may be on a different chain, the V$_H$ domain being part of an immunoglobulin heavy chain or fragment thereof and the V$_L$ being part of an immunoglobulin light chain or fragment thereof.

By "IL-1β binding molecule" is meant any molecule capable of binding to the IL-1β ligand either alone or associated with other molecules. The binding reaction may be shown by standard methods (qualitative assays) including, for example, a bioassay for determining the inhibition of IL-1β binding to its receptor or any kind of binding assays, with reference to a negative control test in which an antibody of unrelated specificity but of the same isotype, e.g. an anti-CD25 antibody, is used. Advantageously, the binding of the IL-1β binding molecules of the invention to IL-1β may be shown in a competitive binding assay.

Examples of antigen binding molecules include antibodies as produced by B-cells or hybridomas and chimeric, CDR-grafted or human antibodies or any fragment thereof, e.g. F(ab')$_2$ and Fab fragments, as well as single chain or single domain antibodies.

A single chain antibody consists of the variable domains of the heavy and light chains of an antibody covalently bound by a peptide linker usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By "chimeric antibody" is meant an antibody in which the constant regions of heavy or light chains or both are of human origin while the variable domains of both heavy and light chains are of non-human (e.g. murine) origin or of human origin but derived from a different human antibody. By "CDR-grafted antibody" is meant an antibody in which the hypervariable regions (CDRs) are derived from a donor antibody, such as a non-human (e.g. murine) antibody or a different human antibody, while all or substantially all the other parts of the immunoglobulin e.g. the constant regions and the highly conserved parts of the variable domains, i.e. the framework regions, are derived from an acceptor antibody, e.g. an antibody of human origin. A CDR-grafted antibody may however contain a few amino acids of the donor sequence in the framework regions, for instance in the parts of the framework regions adjacent to the hypervariable regions. By "human antibody" is meant an antibody in which the constant and variable regions of both the heavy and light chains are all of human origin, or substantially identical to sequences of human origin, not necessarily from the same antibody and includes antibodies produced by mice in which the murine immunoglobulin variable and constant part genes have been replaced by their human counterparts, e.g. as described in general terms in EP 0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0 438474 B1 and EP 0 463151 B1.

The phrase direct equivalents encompasses any molecule, antibody or functional fragment thereof having the properties of an IL-1beta binding molecule of the invention as provided in this description, including antibodies of various species and isotypes, Fab2, Fab and scFv fragments and mutants comprising 1, 2, 3, 4, 5, 6, 7, 8, 9, 10 or more point mutations in the CDR, regions or outside the CDR regions of SEQ ID NO:1 and 2.

Particularly preferred IL-1β binding molecules of the invention are human antibodies especially the ACZ 885 antibody as hereinafter described in the Examples and in WO 02/16436.

Thus in preferred antibodies of the invention, the variable domains of both heavy and light chains are of human origin, for instance those of the ACZ 885 antibody which are shown in SEQ ID NO:1 and SEQ ID NO:2. The constant region domains preferably also comprise suitable human constant region domains, for instance as described in "Sequences of Proteins of Immunological Interest", Kabat E. A. et al, US Department of Health and Human Services, Public Health Service, National Institute of Health.

Hypervariable regions may be associated with any kind of framework regions, though preferably are of human origin. Suitable framework regions are described in Kabat E. A. et al, ibid. The preferred heavy chain framework is a human heavy chain framework, for instance that of the ACZ 885 antibody which is shown in SEQ ID NO:1. It consists in sequence of FR1, FR2, FR3 and FR4 regions. In a similar manner, SEQ ID NO:2 shows the preferred ACZ 885 light chain framework which consists, in sequence, of FR1', FR2', FR3' and FR4' regions.

Accordingly, the invention also provides an IL-1β binding molecule which comprises at least one antigen binding site comprising either a first domain having an amino acid sequence substantially identical to that shown in SEQ ID NO:1 starting with the amino acid at position 1 and ending with the amino acid at position 118 or a first domain as described above and a second domain having an amino acid sequence substantially identical to that shown in SEQ ID NO:2, starting with the amino acid at position 1 and ending with the amino acid at position 107.

Monoclonal antibodies raised against a protein naturally found in all humans are typically developed in a non-human system e.g. in mice, and as such are typically non-human proteins. As a direct consequence of this, a xenogenic antibody as produced by a hybridoma, when administered to humans, elicits an undesirable immune response which is predominantly mediated by the constant part of the xenogenic immunoglobulin. This clearly limits the use of such antibodies as they cannot be administered over a prolonged period of time. Therefore it is particularly preferred to use single chain, single domain, chimeric, CDR-grafted, or especially human antibodies which are not likely to elicit a substantial allogenic response when administered to humans.

In view of the foregoing, a more preferred IL-1β binding molecule of the invention is selected from a human anti IL-1β antibody which comprises at least
   a) an immunoglobulin heavy chain or fragment thereof which comprises (i) a variable domain comprising in sequence the hypervariable regions CDR1, CDR2 and CDR3 and (ii) the constant part or fragment thereof of a human heavy chain; said CDR1 having the amino acid sequence Val-Tyr-Gly-Met-Asn (SEQ ID NO:3), said CDR2 having the amino acid sequence Ile-Ile-Trp-Tyr-Asp-Gly-Asp-Asn-Gln-Tyr-Tyr-Ala-Asp-Ser-Val-Lys-Gly (SEQ ID NO:4), and said CDR3 having the amino acid sequence Asp-Leu-Arg-Thr-Gly-Pro (SEQ ID NO:5) and b) an immunoglobulin light chain or fragment thereof which comprises (i) a variable domain comprising in sequence the hypervariable regions and optionally also the CDR1', CDR2', and CDR3' hypervariable regions and (ii) the constant part or fragment thereof of a human light chain, said CDR1' having the amino acid sequence Arg-Ala-Ser-Gln-Ser-Ile-Gly-Ser-Ser-Leu-His (SEQ ID NO:6), said CDR2' having the amino acid sequence Ala-Ser-Gln-Ser-Phe-Ser (SEQ ID NO:7), and said CDR3' having the amino acid sequence His-Gln-Ser-Ser-Ser-Leu-Pro (SEQ ID NO:8);

and direct equivalents thereof.

Alternatively, an IL-1β binding molecule of the invention may be selected from a single chain binding molecule which comprises an antigen binding site comprising a) a first domain comprising in sequence the hypervariable regions CDR1, CDR2 and CDR3, said CDR1 having the amino acid sequence Val-Tyr-Gly-Met-Asn (SEQ ID NO:3), said CDR2 having the amino acid sequence Ile-Ile-Trp-Tyr-Asp-Gly-Asp-Asn-Gln-Tyr-Tyr-Ala-Asp-Ser-Val-Lys-Gly (SEQ ID NO:4), and said CDR3 having the amino acid sequence Asp-Leu-Arg-Thr-Gly-Pro (SEQ ID NO:5), b) A second domain comprising the hypervariable regions CDR1', CDR2' and CDR3', said CDR1' having the amino acid sequence Arg-Ala-Ser-Gln-Ser-Ile-Gly-Ser-Ser-Leu-His (SEQ ID NO:6), said CDR2' having the amino acid sequence Ala-Ser-Gln-Ser-Phe-Ser (SEQ ID NO:7), and said CDR3' having the amino acid sequence His-Gln-Ser-Ser-Ser-Leu-Pro (SEQ ID NO:8) and c) a peptide linker which is bound either to the N-terminal extremity of the first domain and to the C-terminal extremity of the second domain or to the C-terminal extremity of the first domain and to the N-terminal extremity of second domain;

and direct equivalents thereof.

As it is well known, minor changes in an amino acid sequence such as deletion, addition or substitution of one, a few or even several amino acids may lead to an allelic form of the original protein which has substantially identical properties.

Thus, by the term "direct equivalents thereof" is meant either any single domain IL-1β binding molecule (molecule X)

(i) in which the hypervariable regions CDR1, CDR2 and CDR3 taken as a whole are at least 80% homologous, preferably at least 90% homologous, more preferably at least 95% homologous to the hypervariable regions as shown above and, (ii) which is capable of inhibiting the binding of IL-1β to its receptor substantially to the same extent as a reference molecule having framework regions identical to those of molecule X but having hypervariable regions CDR1, CDR2 and CDR3 identical to those shown in above, or any IL-1β binding molecule having at least two domains per binding site (molecule X')

(i) in which the hypervariable regions CDR1, CDR2, CDR3, CDR1', CDR2' and CDR3' taken as a whole are at least 80% homologous, preferably at least 90% homologous, more preferably at least 95, 98 or 99% homologous, to the hypervariable regions as shown above and (ii) which is capable of inhibiting the binding of IL-1β to its receptor substantially to the same extent as a reference molecule having framework regions and constant parts identical to molecule X', but having hypervariable regions CDR1, CDR2, CDR3, CDR1', CDR2' and CDR3', identical to those shown above.

In a further aspect the invention also provides an IL-1beta binding molecule comprising both heavy ($V_H$) and light chain ($V_L$) variable domains in which said IL-1beta binding molecule comprises at least one antigen binding site comprising:

a) an immunoglobulin heavy chain variable domain ($V_H$) which comprises in sequence hypervariable regions CDR1, CDR2 and CDR3, said CDR1 having the amino acid sequence Ser-Tyr-Trp-Ile-Gly (SEQ ID NO:9), said CDR2 having the amino acid sequence Ile-Ile-Tyr-Pro-Ser-Asp-Ser-Asp-Thr-Arg-Tyr-Ser-Pro-Ser-Phe-Gln-Gly (SEQ ID NO:4), and said CDR3 having the amino acid sequence Tyr-Thr-Asn-Trp-Asp-Ala-Phe-Asp-Ile (SEQ ID NO:10), and b) an immunoglobulin light chain variable domain ($V_L$) which comprises a CDR3' hypervariable region having the amino acid sequence Gln-Gln-Arg-Ser-Asn-Trp-Met-Phe-Pro (SEQ ID NO:11);

and direct equivalents thereof.

In further aspect the invention provides an IL-1beta binding molecule comprising both heavy ($V_H$) and light ($V_L$) chain variable domains in which said IL-1beta binding molecule comprises at least one antigen binding site comprising:

a) an immunoglobulin heavy chain variable domain ($V_H$) which comprises in sequence hypervariable regions CDR1, CDR2 and CDR3, said CDR1 having the amino acid sequence Ser-Tyr-Trp-Ile-Gly (SEQ ID NO:9), said CDR2 having the amino acid sequence Ile-Ile-Tyr-Pro-Ser-Asp-Ser-Asp-Thr-Arg-Tyr-Ser-Pro-Ser-Phe-Gln-Gly (SEQ ID NO:4), and said CDR3 having the amino acid sequence Tyr-Thr-Asn-Trp-Asp-Ala-Phe-Asp-Ile (SEQ ID NO:10), and b) an immunoglobulin light chain variable domain ($V_L$) which comprises in sequence hypervariable regions CDR1', CDR2' and CDR3', said CDR1' having the amino acid sequence Arg-Ala-Ser-Gln-Ser-Val-Ser-Ser-Tyr-Leu Ala (SEQ ID NO:6), said CDR2' having the amino acid sequence Asp-Ala-Ser-Asn-Arg-Ala-Thr (SEQ ID NO:12), and said CDR3' having the amino acid sequence Gln-Gln-Arg-Ser-Asn-Trp-Met-Phe-Pro (SEQ ID NO:11);

and direct equivalents thereof.

In the present description amino acid sequences are at least 80% homologous to one another if they have at least 80% identical amino acid residues in a like position when the sequence are aligned optimally, gaps or insertions in the amino acid sequences being counted as non-identical residues.

The inhibition of the binding of IL-1β to its receptor may be conveniently tested in various assays including such assays are described in WO 02/16436. By the term "to the same extent" is meant that the reference and the equivalent molecules exhibit, on a statistical basis, essentially identical IL-1β binding inhibition curves in one of the assays referred to above. For example, in IL-1β binding molecules of the invention typically have $IC_{50}$s for the inhibition of the binding of IL-1β to its receptor which are within +/−x5 of that of, preferably substantially the same as, the $IC_{50}$ of the corresponding reference molecule when assayed as described above.

For example, the assay used may be an assay of competitive inhibition of binding of IL-1β by soluble IL-1 receptors and the IL-1β binding molecules of the invention.

Most preferably, the IL-1β binding molecule for use according to the invention is an human IL-1 antibody which comprises at least
- a) one heavy chain which comprises a variable domain having an amino acid sequence substantially identical to that shown in SEQ ID NO:1 starting with the amino acid at position 1 and ending with the amino acid at position 118 and the constant part of a human heavy chain; and
- b) one light chain which comprises a variable domain having an amino acid sequence substantially identical to that shown in SEQ ID NO:2 starting with the amino acid at position 1 and ending with the amino acid at position 107 and the constant part of a human light chain.

Most preferably, the IL-1β binding molecule for use according to the invention is ACZ885 (see Example).

The constant part of a human heavy chain may be of the $\gamma_1$, $\gamma_2$, $\gamma_3$, $\gamma_4$, μ, $\alpha_1$, $\alpha_2$, δ or ε type, preferably of the γ type, more preferably of the $\gamma_1$ type, whereas the constant part of a human light chain may be of the κ or λ type (which includes the $\lambda_1$, $\lambda_2$ and $\lambda_3$ subtypes) but is preferably of the κ type. The amino acid sequences of all these constant parts are given in Kabat et al ibid.

An IL-1β binding molecule of the invention may be produced by recombinant DNA techniques as e.g. described in WO 02/16436.

In yet another embodiment of the invention, IL-1beta Compounds may be antibodies which have binding specificity for the antigenic epitope of human IL-1β which includes the loop comprising the Glu 64 residue of mature human IL-1β (Residue Glu 64 of mature human IL-1β ☐ correspond to residue 180 of the human IL-1beta ☐ precursor). This epitope is outside the recognition site of the IL-1beta ☐ receptor and it is therefore most surprising that antibodies to this epitope, e.g. the ACZ 885 antibody, are capable of inhibiting the binding of IL-1β to its receptor. Thus the use of such antibodies for the treatment of Juvenile rheumatoid arthritis and adult rheumatoid arthritis and/or Auto-Inflammatory Syndromes and/or Muckle Wells Syndrome is novel and are included within the scope of the present invention.

Thus in a further aspect the invention includes the use of an antibody to IL-1β which has antigen binding specificity for an antigenic epitope of human IL-1β which includes the loop comprising residue Glu 64 of mature human IL-1β ☐ and which is capable of inhibiting the binding of IL-1β to its receptor for the treatment of Juvenile rheumatoid arthritis or adult rheumatoid arthritis and/or Auto-Inflammatory Syndromes and/or Muckle Wells Syndrome.

In yet further aspects the invention includes:
- i) use of an antibody to IL-1β ☐ which has antigen binding specificity for an antigenic epitope of mature human IL-1β which includes the loop comprising Glu 64 and which is capable of inhibiting the binding of IL-1β to its receptor, for the prevention and/or treatment of Juvenile rheumatoid arthritis or adult rheumatoid arthritis and/or Auto-Inflammatory Syndromes and/or Muckle Wells Syndrome,
- ii) a method for the prevention and/or treatment of Juvenile rheumatoid arthritis or adult rheumatoid arthritis and/or Auto-Inflammatory Syndromes and/or Muckle Wells Syndrome in a patient which comprises administering to the patient an effective amount of an antibody to IL-1β which has antigen binding specificity for an antigenic epitope of mature human IL-1β which includes the loop comprising Glu 64 and which is capable of inhibiting the binding of IL-1β to its receptor;
- iii) a pharmaceutical composition comprising an antibody to IL-1β ☐ which has antigen binding specificity for an antigenic epitope of mature human IL-1β which includes the loop comprising Glu 64 and which is capable of inhibiting the binding of IL-1β to its receptor, in combination with a pharmaceutically acceptable excipient, diluent or carrier; for the treatment of Juvenile rheumatoid arthritis or adult rheumatoid arthritis syndrome and/or Auto-Inflammatory Syndromes and/or Muckle Wells Syndrome.
- iv) use of an antibody to IL-1β ☐ which has antigen binding specificity for an antigenic epitope of mature human IL-1β which includes the loop comprising Glu 64 and which is capable of inhibiting the binding of IL-1β to its receptor, for the preparation of a medicament for the treatment of Juvenile rheumatoid arthritis or adult rheumatoid arthritis syndrome and/or Auto-Inflammatory Syndromes and/or Muckle Wells Syndrome.

For the purposes of the present description an antibody is "capable of inhibiting the binding of IL-1β" if the antibody is capable of inhibiting the binding of IL-1β to its receptor substantially to the same extent as the ACZ 885 antibody, i.e. has a dissociation equilibrium constant ($K_D$) measured e.g. in a standard BIAcore analysis as disclosed in the Example of 10 nM or lower, e.g. 1 nM or lower, preferably 100 pM or lower, more preferably 50 pM or lower.

Thus in a yet further aspect the invention provides the use of an antibody to IL-1β which has a $K_D$ for binding to IL-1β of about 10 nM, 1 nM, preferably 100 pM, more preferably 50 pM or less for the treatment of Juvenile rheumatoid arthritis or adult rheumatoid arthritis syndrome and/or Auto-Inflammatory Syndromes. This aspect of the invention also includes uses methods and compositions for such high affinity antibodies, as described above for antibodies to IL-1β have binding specificity for an antigenic determinant of mature human IL-1β which includes the loop comprising Glu 64.

In the present description the phrase "Juvenile rheumatoid arthritis or adult rheumatoid arthritis syndrome and/or Auto-Inflammatory Syndromes" encompasses all diseases and medical conditions which are part of Juvenile rheumatoid arthritis or adult rheumatoid arthritis syndrome and/or Auto-Inflammatory Syndromes, whether directly or indirectly, in the disease or medical condition, including the causation, development, progress, persistence or pathology of the disease or condition.

In the present description the phrase "Muckle Wells Syndrome" (also "MWS") encompasses all diseases and medical conditions which are part of "Muckle Wells Syndrome", whether directly or indirectly, in the disease or medical condition, including the causation, development, progress, persistence or pathology of the disease or condition.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell antiproliferative agent. For example, the antibodies according to the invention may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, AP23464, AP23675, AP23841, TAFA-93, biolimus-7 or biolimus-9; an ascomycin having immunosuppressive properties, e.g. ABT-281, ASM981, etc.; corticosteroids; cyclo-phosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide □-cyano-(3,4-dihydroxy]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infective agent. Immunomodulatory drugs which are prone to be useful in combination with a compound of the present invention include e.g.

mediators, e.g. inhibitors, of mTOR activity, including rapamycin of formula

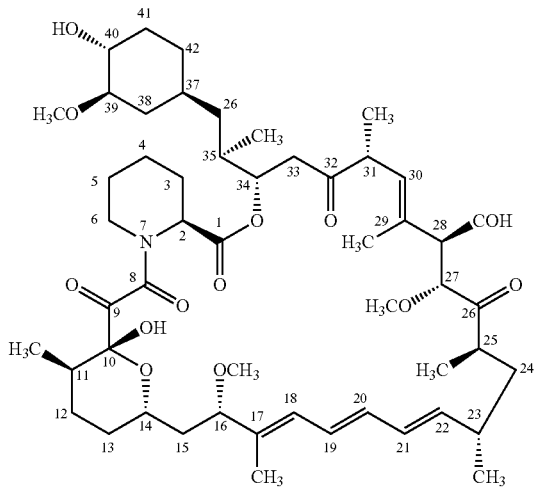

and rapamycin derivatives, e.g. including
40-O-alkyl-rapamycin derivatives, such as 40-O-hydroxyalkyl-rapamycin derivatives, such as 40-O-(2-hydroxy)-ethyl-rapamycin (everolimus), 32-deoxo-rapamycin derivatives and 32-hydroxy-rapamycin derivatives, such as 32-deoxorapamycin,
16-O-substituted rapamycin derivatives such as 16-pent-2-ynyloxy-32-deoxorapamycin, 16-pent-2-ynyloxy-32 (S or R)-dihydro-rapamycin, 16-pent-2-ynyloxy-32(S or R)-dihydro-40-O-(2-hydroxyethyl)-rapamycin,
rapamycin derivatives which are acylated at the oxygen group in position 40, e.g. 40-[3-hydroxy-2-(hydroxymethyl)-2-methylpropanoate]-rapamycin (also known as CCI779), rapamycin derivatives which are substituted in 40 position by heterocyclyl, e.g. 40-epi-(tetrazolyl)-rapamycin (also known as ABT578),
the so-called rapalogs, e. g. as disclosed in WO9802441, WO0114387 and WO0364383, such as AP23573, and compounds disclosed under the name TAFA-93 and biolimus (biolimus A9).

The IL-1beta compounds according to the invention may be administered as the sole active ingredient or in conjunction with bisphosphonates, sequential, simultaneous or combined in one formulation. Bisphosphonates to be used in conjunction with the IL-1beta molecules of the invention comprise etidronate, clodronate, tiludronate, pamidronate, neridronate, olpadronate, alendronate, ibandronate, risedronate, zoledronate, and any salt, acid, polymorph or derivative thereof.

IL-1beta compounds on the invention may advantageously be combined with Protein Kinase C Inhibitors and/or suppressors of T cell activation, in particular indolylmaleimide derivatives such as sotrastaurin (3-(1.H.-indol-3-yl)-4-[2-(4-methyl-piperazin-1-yl)-quinazolin-4-yl]-pyrrole-2,5-dione), for instance in order to inhibit the adaptive immune system and thereby further enhancing the therapeutic effects of IL-1beta compounds.

IL-1beta compounds of the invention may also advantageously be combined with anti-cytokines and/or anti-interleukins, in particular IL-17 binding compounds disclosed in WO2006/013107, optionally in combination with sotrastaurin.

IL-1beta compounds of the invention may advantageously be combined with anti TNFalpha compounds such as etanercept, adalimumab, infliximab, for instance in the treatment of RA and other (auto)-inflammatory diseases.

In the present description the terms "treatment" or "treat" refer to both prophylactic or preventative treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. A successful treatment according to the invention also includes remissions of all reparable symptoms but no remissions of irreparable symptoms. E.g. one of the symptoms of Muckle-Wells is the progressive nerve deafness which is normally irreparable and thus there is no expectation that this symptom may be treated. However, other reparable symptoms of Muckle-Wells such as skin rash, muscle pain fever, fatigue and conjunctivitis may be completely disappear in a successful treatment according to the invention. Another measure of a successful treatment is the decrease of relevant biomarkers for Auto-Inflammatory Syndromes, e.g. Muckle-Wells, i.e. the decrease of serum amyloid protein (SAA) and c-reactive protein (CRP) to normal range, i.e. <10 mg per L serum in patients.

In the present description, the disease "Muckle-Wells" is among others (molecular pathology) determined according to its clinical symptoms which are acute febrile inflammatory episodes of arthritis and urticaria, progressive nerve deafness and optionally long term multi organ amyloidosis (about 25% of cases). Molecular pathology is caused by one or several mutations in the MEFV gene, located on chromosome 16p13, which codes for the protein named pyrin. IL-1β binding molecules as defined above, in particular IL-1β binding molecules according to the first and second aspects of the invention antibodies which have binding specificity for the antigenic epitope of mature human IL-1β which includes the loop comprising Glu 64, in particular antibodies which are capable of inhibiting the binding of IL-1β to its receptor; and antibodies to IL-1β which have a $K_D$ for binding to IL-1β of about 10 nM, 1 nM, preferably 100 pM, more preferably 50 pM or less are herein referred to as Antibodies of the Invention.

In yet another embodiment of the invention, the further uses of the IL-1beta Compounds, e.g. the Antibodies of the Invention are as follows:

Prevention and treatment of Inflammatory Bowel Disease (IBD), Juvenile arthritis, reactive arthritis, ankylosing spondylitis, coronary syndrome, arterial restenosis, cystic fibrosis, Alzheimer's disease, multiple myeloma, arteriosclerosis, pulmonary fibrosis, Muckle-Wells and Chronic Obstructive Pulmonary Disease (COPD).

For all indications disclosed herein this description (Indications of the inventions), the appropriate dosage will, of course, vary depending upon, for example, the particular IL-1beta Compounds, e.g. the Antibody of the Invention to be employed, the host, the mode of administration and the nature and severity of the condition being treated. However, in prophylactic use, satisfactory results are generally indicated to be obtained at dosages from about 0.05 mg to about 10 mg per kilogram body weight more usually from about 0.1 mg to about 5 mg per kilogram body weight. Antibody of the Invention is conveniently administered parenterally, intravenously, e.g. into the antecubital or other peripheral vein, intramuscularly, or subcutaneously.

In yet another embodiment, the invention concerns a surprising frequency of dosing for therapeutic uses, i.e. the treatment schedule with IL-1beta Compounds, preferably IL-1beta antibodies, more preferably ACZ885 (at a typical dose, e.g. between about 0.1 mg to about 50 mg, more preferably between 0.5 mg to 20 mg, even more preferably from 1 mg to 10 mg, of ACZ885 per kg body weight of the patient) may be once every week or less frequently, more preferably once every 2 weeks or less frequently, more preferably once every 3 weeks or less frequently, more preferably once every month or less frequently, more preferably once every 2 months or less frequently, more preferably once every 3 months or less frequently, even more preferably once every 4 months or less frequently, even more preferably once every 5 months or less frequently, or even more preferably once every 6 months or less frequently. Most preferred is once every month.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

The invention is further described by way of illustration in the following Examples.

EXAMPLES

Example 1: ACZ885

Structure and making of ACZ885 are e.g. described in WO 02/16436. In short, the amino-terminal sequences of heavy and light chain variable domains and the corresponding DNA sequences are given in SEQ ID NO:1 and SEQ ID NO:2.

Example 2: Biochemical and Biological Data of ACZ885

The monoclonal antibody ACZ885 is found to neutralize the activity of interleukin-1β in vitro. The monoclonal antibody is further characterized for its binding to recombinant human IL-1β by surface plasmon resonance analysis. The mode of neutralization is assessed by competitive binding studies with soluble IL-1 receptors. The biological activity of the antibody ACZ 885 towards recombinant and naturally produced IL-1β is determined in primary human cell, responsive to stimulation by IL-1β.

Determination of Dissociation Equilibrium Constant

The association and dissociation rate constants for the binding of recombinant human IL-1beta to ACZ885 are determined by surface plasmon resonance analysis. ACZ885 is immobilized, and binding of recombinant IL-1beta in a concentration range from 1 to 4 nM is measured by surface plasmon resonance. The chosen format represents a monovalent interaction and thus permits treating the binding event of IL-1beta to ACZ885 according to a 1:1 stoichiometry. Data analysis is performed using the BIAevaluation software.

| | $k_{on}$ [$10^5$/Ms] | $k_{off}$ [$10^{-5}$/s] | $K_D$ [pM] | |
|---|---|---|---|---|
| ACZ885 | 11.0 +/− 0.23 | 3.3 +/− 0.27 | 30.5 +/− 2.6 | n = 22 |

Conclusion: ACZ885 binds to recombinant human IL-1beta with very high affinity.

Example 3: Clinical Trial with ACZ885

In order to asses the suitability of an IL-1beta Compound, e.g. ACZ885, an open-label, single center dose titration study of ACZ885 (human anti-IL-1beta monoclonal antibody) to assess the clinical efficacy, safety, pharmacokinetics and pharmacodynamics in patients with MW syndrome, characterized by NALP3 mutations, is conducted.

Patients are treated by a single dose infusion of ACZ885 (10 mg/kg i.v.). Clinical response is measured by improvement of symptoms (e.g., skin rash, muscle pain, fever, fatigue) and by lowering of acute phase proteins serum amyloid protein (SAA) and c-reactive protein (CRP). In addition, response to treatment is assessed by the analysis of mRNA obtained from peripheral blood cells. A second treatment (1 mg/kg i.v.) is given after re-appearance of clinical symptoms. Results: Clinical remission of symptoms (fever, rash, conjunctivitis) within 3 days, and decrease of CRP and SAA to normal range (<10 mg/L) in patients.

Clinical remission of symptoms with first infusion lasts for at least 134 days, typically between 160 and 200 days. Upon second treatment with lower dose, patients respond with improvement of symptoms and normalization of acute phase proteins.

Analysis of mRNA obtained from peripheral blood cells demonstrates down-regulation of the transcription of IL-1β and IL-1β-induced genes within 24 h upon treatment with ACZ885. This suggests that ACZ885 is capable to interrupt a positive feedback loop in vivo which leads to self-sustained overproduction of IL-1β in these patients. This contention is also supported by initial characterization of PK/PD effects of ACZ885 which demonstrates the blockade of production of IL-1β upon treatment with ACZ885 in these patients. This particular ability of ACZ885 may contribute (be causal) for its long-lasting clinical effect.

What is claimed:

1. A method of treating an auto-inflammatory syndrome in a patient in need thereof, comprising administering to said patient an effective amount of an IL-1beta binding antibody comprising an immunoglobulin $V_H$ comprising the amino acid sequence set forth as SEQ ID NO:1 and an immunoglobulin $V_L$ comprising the amino acid sequence set forth as SEQ ID NO:2.

2. A method of treating an auto-inflammatory syndrome in a patient in need thereof, comprising administering to said patient an effective amount of an IL-1beta binding antibody comprising both heavy ($V_H$) and light chain ($V_L$) variable domains, wherein said IL-1beta binding antibody comprises at least one antigen binding site comprising:
   a) an immunoglobulin heavy chain variable domain ($V_H$) which comprises in sequence hypervariable regions CDR1, CDR2 and CDR3, said CDR1 having the amino acid sequence Val-Tyr-Gly-Met-Asn (SEQ ID NO: 3), said CDR2 having the amino acid sequence Ile-Ile-Trp-Tyr-Asp-Gly-Asp-Asn-Gln-Tyr-Tyr-Ala-Asp-Ser-Val-Lys-Gly (SEQ ID NO:4), and said CDR3 having the amino acid sequence Asp-Leu-Arg-Thr-Gly-Pro (SEQ ID NO:5), and
   b) an immunoglobulin light chain variable domain ($V_L$) which comprises in sequence hypervariable regions CDR1', CDR2' and CDR3', said CDR1' having the amino acid sequence Arg-Ala-Ser-Gln-Ser-Ile-Gly-Ser-Ser-Leu-His (SEQ ID NO:6), said CDR2' having the amino acid sequence Ala-Ser-Gln-Ser-Phe-Ser (SEQ ID NO:7), and said CDR3' having the amino acid sequence His-Gln-Ser-Ser-Ser-Leu-Pro (SEQ ID NO:8).

3. The method according to claim 1, wherein the IL-1beta binding antibody is a monoclonal human antibody.

4. The method according to claim 3, wherein the auto-inflammatory syndrome is Juvenile rheumatoid arthritis.

5. The method according to claim 4, wherein the IL-beta binding antibody is administered once every week once every 2 weeks, once every 3 weeks, once every month, once every 2 months, once every 3 months, once every 4 months, once every 5 months, or once every 6 months.

6. The method according to claim 5, wherein the IL-beta binding antibody is administered subcutaneously.

7. The method according to claim 3, wherein the auto-inflammatory syndrome is latent autoimmune diabetes in adults (LADA).

8. The method according to claim 3, wherein the auto-inflammatory syndrome is chronic infantile neurological cutaneous articular (CINCA) syndrome.

9. The method according to claim 3, wherein the auto-inflammatory syndrome is adult rheumatoid arthritis syndrome.

10. The method according to any of claims 7-9, wherein the IL-beta binding antibody is administered once every week, once every 2 weeks, once every 3 weeks, once every month, once every 2 months, once every 3 months, once every 4 months, once every 5 months, or once every 6 months.

11. The method according to claim 10, wherein the IL-beta binding antibody is administered subcutaneously.

12. The method according to claim 6 or 11, wherein the IL-beta binding antibody is administered at a dose between 0.05 mg-10 mg per kg body weight of the patient.

13. The method according to claim 12, wherein the IL-beta binding antibody is administered at a dose between 1 mg-10 mg per kg body weight of the patient.

14. The method according to claim 12, wherein the IL-beta binding antibody is administered at a dose between 0.1 mg-5 mg per kg body weight of the patient.

15. The method according to claim 12, wherein the IL-beta binding antibody is administered in a liquid pharmaceutical formulation.

16. The method according to claim 13 or claim 14, wherein the IL-beta binding antibody is administered in a liquid pharmaceutical formulation.

17. The method according to claim 15, wherein the IL-beta binding antibody is ACZ885.

18. The method according to claim 16, wherein the IL-beta binding antibody is ACZ885.

* * * * *